United States Patent [19]

Suda et al.

[11] Patent Number: 4,596,825

[45] Date of Patent: Jun. 24, 1986

[54] METHOD OF TREATING LIVER DISTURBANCES RESULTING FROM ALCOHOL CONSUMPTION AND A COMPOSITION THEREFOR

[75] Inventors: Tomio Suda, Tachikawa; Masaharu Horiguchi, Mitaka, both of Japan

[73] Assignee: Ajinomoto Co., Inc., Tokyo, Japan

[21] Appl. No.: 762,281

[22] Filed: Aug. 5, 1985

[30] Foreign Application Priority Data

Aug. 20, 1984 [JP] Japan ................ 59-172793

[51] Int. Cl.$^4$ .......................................... A61K 31/195
[52] U.S. Cl. ........................ 514/561; 514/811
[58] Field of Search ........................ 514/561, 811

[56] References Cited

U.S. PATENT DOCUMENTS 3,950,529  4/1976  Fischer et al. .............. 514/561
4,279,917  7/1981  Tokami et al. ............... 514/561

*Primary Examiner*—Stanley J. Friedman
*Attorney, Agent, or Firm*—Oblon, Fisher, Spivak, McClelland & Maier

[57] ABSTRACT

A pharmaceutical composition for preventing or alleviating the effects of acute alcoholism, in particular liver disturbances in mammals, which comprises a mixture of alanine or a pharmaceutically acceptable salt or derivative thereof capable of effectively acting as alanine in vivo or a mixture thereof, and ornithine or a pharmaceutically acceptable salt or derivative thereof capable of effectively acting as ornithine in vivo or a mixture thereof in a ratio such that the amount of ornithine present in said mixture is at least about 1/1000 the amount of alanine present, both of said ornithine and alanine being present in an amount effective to prevent or alleviate said effects.

14 Claims, No Drawings

METHOD OF TREATING LIVER DISTURBANCES RESULTING FROM ALCOHOL CONSUMPTION AND A COMPOSITION THEREFOR

BACKGROUND OF THE INVENTION

1. Field of the Invention:

This invention relates to a method of treating liver disturbances resulting from alcohol consumption and a composition therefor.

2. Description of the Background:

Alcoholic liver disturbances give rise to symptoms of varying severity including a disturbance of consciousness to a mild degree, coma, numbness and, finally, death due to acute alcoholism.

For purposes of alleviating or treating such alcoholic liver disturbances, protoporphyrin preparations, gluconic acid preparations and amino acid preparations such as arginine hydrochloride, etc. have been employed heretofore.

Additionally, with respect to amino acids, it is also known that the administration of branched amino acids such as valine, leucine, isoleucine, etc., especially valine, are effective in treating patients with hepatic coma. See Published Examined Japanese Patent Application No. 29446/82. It is also known that ornithine improves detoxification and excretion of ammonia in the liver in hepatic coma.

Further, it is also known that a salt of ornithine with adenosine triphosphoric acid promotes the detoxification and excretion of the above-mentioned ammonia. See Published Examined Japanese Patent Application No. 9316/66.

Metabolic changes in liver functions due to alcohol consumption can be severe. While some limited therapeutic measures have been effected using drugs, largely as preventative measures, no measures have been suggested to date for alleviating the results of such metabolic changes once they have occurred.

Therefore, a need continues to exist for a method by which the damaging effects caused by metabolic changes in liver functions due to alcohol consumption can be alleviated.

SUMMARY OF THE INVENTION

Accordingly, it is an object of the present invention to provide a method for treating alcoholic liver disturbances in mammals in a safe and effective manner.

It is also an object of the present invention to provide a method for preventing alcoholic liver disturbances in mammals in a safe and effective manner.

Further, it is also an object of this invention to provide a pharmaceutical composition for preventing and alleviating alcoholic liver disturbances in mammals in a safe and effective manner.

According to the present invention, the foregoing and other objects are attained by providing a pharmaceutical composition for treating or alleviating alcoholic liver disturbances in mammals which contains alanine or a pharmaceutically acceptable salt or other derivative thereof capable of effectively acting as alamine in vivo or a mixture thereof and ornithine or a pharmaceutically acceptable salt or other derivative thereof capable of effectively acting as ornithine in vivo or a mixture thereof in a molar concentration ratio of not less than about 1:0.001.

DETAILED DESCRIPTION OF THE PREFERRED EMBODIMENTS

According to the present invention, it has now been found that mixtures of alanine and ornithine exhibit a surprising effect in alleviating disturbances in the liver tissues of alcoholic mammals. Moreover, a surprising effect in alleviating disturbances or interruptions in consciousness in alcoholic mammals is also observed. These effects are quite surprising, particularly in view of the fact that such effects are not observed when administering either alanine or ornithine alone. Thus, according to the present invention, the alanine and ornithine must be used in combination.

The optimum ratio of alanine and ornithine to be used in combination varies depending upon, for example, the dose of alanine and the desired effect. In general, however, an acceptable ratio of alanine and ornithine in combination is not less than about 1/1000 moles of ornithine per alanine. There is no upper limit for the quantity of ornithine to alanine but where the dose of alanine is constant, no proportional increase in the effect is noted even when the dose of ornithine to be given in combination is increased. Rather, such increases in ornithine content are undesirable for the functional and economical reasons. Accordingly, mainly due to functional and economical reasons, the upper limit of ornithine to alanine to be used in combination is about 10 moles of the former per mole of the latter. On the other hand, the lower limit of ornithine to alanine is about 1/1000 the number of moles of alanine since the effects of the present invention are observed even exhibited with a small quantity of ornithine. However, the effects are not observed with a quantity of less than about that quantity. Accordingly, it is preferred that the ratio of ornithine to alanine be used in a combination of molar ratios of about 1:0.001 to 10 preferably 1:0.05 to 0.5.

Alanine and ornithine may be used in the form of salts thereof or other pharmaceutically acceptable derivatives thereof as long as they effectively act as alanine and ornithine in vivo. Specific examples of preferred combinations include L-alanine and L-ornithine, DL-alanine and L-ornithine, L-alanine and L-ornithine hydrochloride, DL-alanine and L-ornithine hydrochloride, etc.

The composition of the present invention may be provided in the form of drugs or foodstuffs. The drugs may be orally, parenterally or intraperitoneally administered.

The compositions of the present invention may be provided in the form of powders, granules, tablets, sugar-coated pills, capsules, liquids, etc. for oral administration, and in the form of suspensions, liquids, emulsions, ampules, injections or combinations thereof for parenteral administration. As diluting agents for combination with the present compositions, solid, semi-solid or liquid forms may be used. Examples of the same include water, gelatin, sugars, starch, fatty acids and salts thereof, alcohols, oils and fats, talc, physiological saline, etc. or a combination of two or more. According to the present invention, the ratio of the total weight of alanine, ornithine and/or salts thereof in such compositions may be generally from about 0.01 to 100 wt %.

Moreover, the compositions of the present invention should be administered in such amounts that the dosages of alanine and ornithine are provided to the mammal being treated in amounts effective to elicit the effects thereof. However, it has been found advantageous to use compositions such that alanine and ornithine are provided to the mammal in the amount of about 1-5 mmol/kg of body weight of alanine and 0.001-50 mmol/kg of body weight of ornithine. It is even better, however, to use amounts such that about 2-4 mmol/kg of body weight of alanine and 0.002-40 mmol/kg of body weight or ornithine are provided. Particularly preferred, however, are dosages of about 2.5 mmol/kg of body weight of alanine and 0.625 mmol/kg of body weight of ornithine.

On the other hand, the composition of the present invention may be advantageously provided as foodstuffs. Preferred modes for the foodstuffs are those that are taken together with, prior to or after consuming alcohols. Specific examples of such foodstuffs include smoked foodstuffs, shreds of dried cuttlefish, salted fish guts, Karasumi or salted and dried roe, salmon roe, walleye pollack roe, salted pollack roe, cavier, foie glas, rotten milk, tofu or soybean curds, cheese, potato chips, rice cake, bean cake and other high protein foodstuffs, high oil-and-fat foodstuffs or high starch foodstuffs generally used as so-called relishes taken with sake; or sauce of grilled meat, soysauce for Sashimi, sauce for boiled bean curds or tofu served cold, sauces such as dressing, mayonnaise, etc., seasonings such as Rha oil, vinegar, table salt, etc.; alcoholic drinks such as Sake, beer, Shochu, wine, whisky, grandy, samshu, gin, rum, campari, vermouth, various cocktails, etc.; sport drinks, tomato juice and other juices, or soft drinks such as coke, for example.

The ratio of the total weight of alanine, ornithine and/or salts thereof is generally from about 0.01 to 10% in the foodstuffs of the present invention. Where the use of the amino acids of the present invention in a high concentration are not preferred, the amino acids may be used after they are encapsuled, for example in oils and fats, proteins, starch, etc., having a relatively high melting point. Also, masking agents can be used, preferably, in combination thererwith.

The composition of the present invention contains alanine and ornithine as essential effective components but needless to say, other amino acids may also be present without departing from the object of the present invention.

By the administration of the composition of the present invention containing alanine and ornithine, a potent lifesaving effect is obtained as is seen in tests involving acute ethanol intoxication. Alleviation of the liver tissue disturbance symptoms is also noted. The disturbance or loss of consciousness due to the administration of ethanol is reduced by administration of the composition of the present invention. The capability of removing ethanol in blood is also accelerated by administration of the composition of the present invention. Further, a significant increase in blood sugar after administration of ethanol is also noted in mammals to which the composition of the present invention is administered. It is believed that accelerated neogenesis of such sugars indicates that the administration of ornithine, said to accelerate the urea cycle, is necessary when ethanol is administered. In relation to sugar neogenesis in the urea cycle and the metabolism of ethanol, etc., the lifesaving effect is due to the administration of alanine and ornithine in combination.

The present invention will now be further illustrated by certain examples and references which are provided for purposes of illustration only and are not intended to limit the present invention.

EXAMPLE 1

Experiment on Acute Ethanolism of Mice:
Method:

Using mice of the JCI:ICR strain of about six (6) weeks age, test substances (0.1 to 0.125 M in 0.9% NaCl solution; pH 7.4) shown in Tables 1 and 2 were intraperitoneally injected after 20 hours of fasting. As a control, the same quantity of a 0.9% NaCl solution was interperitoneally injected. About 40 minutes after, 170 mmol/kg of a 19% W/V ethanol solution in 0.9% NaCl solution was intraperitoneally injected and the survival rate for the subsequent 5 days was observed.

As shown in Tables 1 and 2, the survival rate was 35% with a control group of 40 mice. Various amino acids, glucose and various organic acids were scrutinized for possible advantageous detoxifying effects. Amino acids such as alanine, threonine, leucine, isoleucine, etc., exhibited a modest lifesaving effect. With alanine alone, the survival rate increased to 67%. However, when administering alanine in combination with a small quantity of ornithine, the survival rate markedly increased to 100%. With administration of ornithine alone no increase in the survival rate was noted. With respect to the group to which alanine and ornithine was administered (AO administration), a large increase in body weight was observed as compared to the control group. Upon examining the liver tissue patterns of the control group, degenerated and swollen liver cells were remarkably observed around the central vein by H-E staining. But in the AO administration group, such liver tissue disturbances were alleviated and no such observations were made.

TABLE 1

Survival Rate in Single Administration of Amino Acids, Organic Acids or Glucose

| Substance | Concentration (M) | Dose mmol/kg b.w. | Dose mg/kg b.w. | Number of Mice used | Number of Dead Mice | Alive Mice Number | Alive Mice % |
|---|---|---|---|---|---|---|---|
| 0.9% NaCl Solution (control) | — | — | — | 40 | 26 | 14 | 35 |
| L-α-Alanine | 0.1 | 2.5 | 222.7 | 15 | 5 | 10 | 67 |
| L-Threonine | 0.1 | 2.5 | 297.8 | 12 | 4 | 8 | 67 |
| L-Leucine | 0.1 | 2.5 | 327.9 | 10 | 4 | 6 | 60 |
| L-Isoleucine | 0.1 | 2.5 | 327.9 | 12 | 3 | 9 | 75 |
| L-Cysteine | 0.1 | 2.5 | 302.9 | 12 | 4 | 8 | 67 |
| L-Glutamic acid | 0.1 | 2.5 | 367.8 | 16 | 6 | 9 | 56 |
| L-Methionine | 0.1 | 2.5 | 373.0 | 12 | 6 | 6 | 50 |
| L-arginine | 0.1 | 2.5 | 435.5 | 10 | 6 | 4 | 40 |
| L-Valine | 0.1 | 2.5 | 292.9 | 10 | 6 | 4 | 40 |
| L-Lysine.HCl | 0.1 | 2.5 | 456.6 | 10 | 7 | 3 | 30 |
| L-Aspartic acid | 0.1 | 2.5 | 332.7 | 10 | 7 | 3 | 30 |
| L-Glycine | 0.1 | 2.5 | 187.7 | 10 | 10 | 0 | 0 |

TABLE 1-continued

Survival Rate in Single Administration of Amino Acids, Organic Acids or Glucose

| Substance | Concentration (M) | Dose mmol/kg b.w. | Dose mg/kg b.w. | Number of Mice used | Number of Dead Mice | Alive Mice Number | Alive Mice % |
|---|---|---|---|---|---|---|---|
| L-Serine | 0.1 | 2.5 | 262.7 | 10 | 10 | 0 | 0 |
| L-Tryptophane | 0.025 | 1.25 | 255.3 | 10 | 10 | 0 | 0 |
| L-Phenylalanine | 0.1 | 2.5 | 422.8 | 10 | 10 | 0 | 0 |
| L-Ornithine | 0.1 | 2.5 | 330.4 | 10 | 6 | 4 | 40 |
| α-Ketoglutaric acid | 0.1 | 2.5 | 365.3 | 10 | 6 | 4 | 40 |
| L-Malic acid | 0.1 | 2.5 | 335.2 | 10 | 10 | 0 | 0 |
| Oxaloacetic acid | 0.1 | 2.5 | 330.2 | 10 | 10 | 0 | 0 |
| Pyruvic acid | 0.1 | 2.5 | 220.2 | 10 | 7 | 3 | 30 |
| Glucose | 0.1 | 2.5 | 450.4 | 10 | 6 | 4 | 40 |

TABLE 2

Survival Rate in Administration of Amino Acids in Combination

| Substance | Concentration (M) | Dose mmol/kg b.w. | Dose mg/kg b.w. | Number of Mice used | Number of Dead Mice | Alive Mice Number | Alive Mice % |
|---|---|---|---|---|---|---|---|
| 0.9% NaCl Solution (control) | — | — | — | 12 | 8 | 4 | 33 |
| L-α-Alanine | 0.1 | 2.5 | 222.7 | 20 | 0 | 20 | 100 |
| L-Ornithine | 0.025 | 0.625 | 85.9 | | | | |
| L-Threonine | 0.1 | 2.5 | 297.8 | 10 | 6 | 4 | 40 |
| L-Ornithine | 0.025 | 0.625 | 85.9 | | | | |
| L-Aspartic acid | 0.1 | 2.5 | 332.7 | 12 | 8 | 4 | 33 |
| L-Ornithine | 0.025 | 0.625 | 85.9 | | | | |
| L-Glutamic acid | 0.1 | 2.5 | 367.8 | 12 | 6 | 6 | 50 |
| L-Ornithine | 0.025 | 0.625 | 85.9 | | | | |
| L-Leucine | 0.1 | 2.5 | 327.9 | 10 | 8 | 2 | 20 |
| L-Ornithine | 0.025 | 0.625 | 85.9 | | | | |

EXAMPLE 2

The disturbance of consciousness caused by the administration of ethanol and, the blood sugar content and the influence of amino acids on ethanol in the blood were examined under the same conditions as in Example 1 except that ethanol was administered in an amount of 100 mmol/kg body weight, somewhat smaller than in Example 1. The results evidence that when coma or numbness of mice was observed after the administration of ethanol, the degree of disturbance of consciousness was markedly alleviated with the AO composition administration group but with the groups to which alanine or ornithine was administered singly, no such an effect was noted. Under the same conditions as in this example, blood was collected from the eyeground and, the blood sugar content and the change in ethanol content in the blood were examined. As compared to the control group, the rate of removing ethanol in blood was accelerated with the AO composition administration group. However, such an effect was not noted with the groups to which alanine or ornithine was administered singly. Further with the AO composition administration group, the blood sugar value gradually increased after administration of ethanol, resulting in a significantly higher value than with the other groups.

TABLE 3

Survival Rate in acute Ethanolism depending on Dose of Ethanol Given

| Substance | Concentration % (W/V) | Dose mmol/kg body weight | Dose mmol/kg body weight | Number of mice used | Number of dead mice | Time of Coma | Alive Mice Number | Alive Mice % |
|---|---|---|---|---|---|---|---|---|
| Ethanol | 19 | 70 | 3.25 | 10 | 0 | ca. 80 mins. | 10 | 100 |
| Ethanol | 19 | 105 | 4.87 | 10 | 0 | ca. 3 hrs. | 10 | 100 |
| Ethanol | 19 | 142 | 6.5 | 10 | 4 | ca. 18 hrs. | 6 | 60 |
| Ethanol | 19 | 170 | 7.8 | 10 | 6 | ca. 30 hrs. | 4 | 40 |
| Ethanol | 19 | 211 | 9.75 | 5 | 5 | ∞ | 0 | 0 |
| Ethanol | 19 | 282 | 13.0 | 5 | 5 | ∞ | 0 | 0 |

Mice used: Mice of JCI:ICR strain aging about 4 weeks
Method:
(I) Fasted for about 20 hours (accessible to water)
(II) Each amount of ethanol in 0.9% NaCl solution (19% W/V) was intraperitoneally injected.
(III) Time of coma subsequently occurred and survival rate for 5 days after II.

EXAMPLE 3

The lifesaving effect of the composition of the present invention was examined vis a vis acute ethanol alcoholism by administration of alanine and ornithine in combination. The mice used and method were the same as in the above Examples.

As shown in Table 4, the results indicate that a marked lifesaving effect was noted when administering alanine and ornithine in combination. In particular, the survival rate was 100% when the mole concentration ratio of alanine to ornithine was 1:0.25.

TABLE 4

| Substance | Concentration (M) | Dose mmol/kg b.w. | Dose mg/kg b.w. | Number of Mice used | Number of Dead Mice | Alive Mice Number | Alive Mice % |
|---|---|---|---|---|---|---|---|
| 0.9% NaCl solution (control) | — | — | — | 10 | 6 | 4 | 40 |
| L-α-Alanine | 0.1 | 2.5 | 222.7 | 10 | 0 | 10 | 100 |
| L-Ornithine | 0.025 | 0.625 | 85.9 | | | | |
| L-α-Alanine | 0.2 | 5.0 | 445.4 | 10 | 1 | 9 | 90 |
| L-Ornithine | 0.025 | 0.625 | 85.9 | | | | |
| L-α-Alanine | 0.12 | 3.0 | 267.2 | 10 | 1 | 9 | 90 |
| L-Ornithine | 0.012 | 0.3 | 39.6 | | | | |
| L-α-Alanine | 0.12 | 3.0 | 267.2 | 10 | 1 | 9 | 90 |
| L-Ornithine | 0.025 | 0.625 | 85.9 | | | | |
| L-α-Alanine | 0.12 | 3.0 | 267.2 | 10 | 1 | 9 | 90 |
| L-Ornithine | 0.05 | 1.25 | 165.2 | | | | |

The composition of the present invention was also encapsulated in solid fat and was added to a commercially available sport drink in such a manner that the contents of alanine and ornithine were 5 g/dl and 1.5 g/dl, respectively. Thus, sport drink containing alanine and ornithine was prepared.

The sport drink so obtained was intraperitoneally injected to mice under the same conditions as in Example 2. With other conditions being identical, the disturbance of consciousness due to the administration of ethanol was examined and also the blood sugar content and the effect on the ethanol content in the blood due to the administration of amino acids was examined. The extent to which consciousness was disturbed by alcohol consumption was remarkably reduced with the group to which the sport drink containing the composition of the present invention was administered, as compared to the control group.

While the compositions and method of the present invention will be seen to be generally useful for all mammals, the compositions and method of the present invention have particular utility in treating acute ethanolism and liver disturbances therefrom in humans.

Having now fully described the present invention, it will be apparent to one of ordinary skill in the art that many changes and modifications can be made thereto without departing from the spirit or scope of the invention as set forth herein.

What is claimed as new and desired to be secured by Letters Patent of the United States is:

1. A method of preventing or alleviating alcoholic liver disturbances in mammals which comprises administering to said mammal a pharmaceutical composition consisting essentially of alanine or a pharmaceutically acceptable salt or other derivative thereof capable of effectively acting as alanine in vivo or a mixture thereof, and ornithine or a pharmaceutically acceptable salt or other derivative thereof capable of effectively acting as ornithine in vivo or a mixture thereof in a ratio such that the molar ratio of ornithine to alanine in said mixture is about 1:0.001 to 10, both of said ornithine and alanine being present in an amount effective to prevent or alleviate said alcoholic liver disturbance.

2. The method of claim 1, wherein said alcoholic liver disturbances comprise loss of consciousness and degeneration and swelling of liver cells.

3. The method of claim 1, wherein said composition is administered orally, parenterally or intraperitoneally.

4. The method of claim 3, wherein said mixture is administered in an amount such that alanine and ornithine are provided to said mammal in the amount of about 1–5 mmol/kg of body weight and about 0.001–50 mmol/kg of body weight, respectively.

5. The method of claim 4, wherein said mixture is administered in an amount such that alanine and ornithine are provided to said mammal in the amount of about 2.5 mmol/kg of body weight and about 0.625 mmol/kg of body weight, respectively.

6. The method of claim 1, wherein said mammal is a human.

7. A pharmaceutical composition for preventing or alleviating alcoholic liver disturbances in mammals, which consists essentially of a mixture of alanine or a pharmaceutically acceptable salt or other derivative thereof capable of effectively acting as alanine in vivo, or a mixture thereof, and ornithine or a pharmaceutically acceptable salt or other derivative thereof capable of effectively acting as ornithine in vivo, or a mixture thereof in a ratio such that the molar ratio of ornithine to alanine in said mixture is about 1:0.001 to 10, both of said ornithine and alanine being present in an amount effective to prevent or alleviate said alcoholic liver disturbances.

8. The pharmaceutical composition of claim 1, wherein the ratio of ornithine to alanine is in the range of 0.05–0.5 to 1.

9. The pharmaceutical composition of claim 1, wherein the ratio of ornithine to alanine is in the range of 0.25 to 1.

10. The pharmaceutical composition of claim 1, wherein said mixture comprises L-alanine and L-ornithine, or DL-alanine and L-ornithine, or L-alanine and L-ornithine hydrochloride and DL-alanine and L-ornithing hydrochloride.

11. The pharmaceutical composition of claim 1, wherein said alanine and ornithine mixture comprises about 0.01 to 100% by weight of the total composition weight.

12. The pharmaceutical composition of claim 1, which further comprises water, gelatin, sugars, starch, fatty acids and salts thereof, alcohols, oils, fats, talc or physiological saline solution or a mixture of two or more.

13. A foodstuff comprising the mixture of claim 1.

14. The foodstuff according to claim 3, comprising 0.01–10% by weight of said mixture.

* * * * *